(12) United States Patent
Zhou et al.

(10) Patent No.: US 8,507,054 B2
(45) Date of Patent: Aug. 13, 2013

(54) MEDIA FOR INKJET PRINTING

(75) Inventors: Xiaoqi Zhou, San Diego, CA (US);
Douglas E. Knight, San Diego, CA (US); Hai Quang Tran, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 105 days.

(21) Appl. No.: 12/995,315

(22) PCT Filed: May 30, 2008

(86) PCT No.: PCT/US2008/065390
§ 371 (c)(1),
(2), (4) Date: Nov. 30, 2010

(87) PCT Pub. No.: WO2009/145790
PCT Pub. Date: Dec. 3, 2009

(65) Prior Publication Data
US 2011/0104406 A1    May 5, 2011

(51) Int. Cl.
| | |
|---|---|
| B41M 5/00 | (2006.01) |
| B41M 5/52 | (2006.01) |
| B41M 5/50 | (2006.01) |
| C04B 41/00 | (2006.01) |
| C04B 41/52 | (2006.01) |
| A61F 2/30 | (2006.01) |
| C23C 30/00 | (2006.01) |

(52) U.S. Cl.
CPC .............. B41M 5/5218 (2013.01); B41M 5/52 (2013.01); B41M 5/506 (2013.01); B41M 5/5245 (2013.01); C04B 41/009 (2013.01); C04B 41/52 (2013.01); A61F 2/30767 (2013.01); C23C 30/005 (2013.01)
USPC ........ 428/32.21; 428/32.3; 428/689; 428/698

(58) Field of Classification Search
CPC ...... B41M 5/5218; B41M 5/52; B41M 5/506; B41M 5/5245; C04B 41/009; C04B 41/52; A61F 2/20767; C23C 30/005
USPC .............................. 428/32.21, 32.3, 689, 698
See application file for complete search history.

(56) References Cited

U.S. PATENT DOCUMENTS

| | | | |
|---|---|---|---|
| 4,132,553 A * | 1/1979 | Burkle et al. ................. | 430/146 |
| 5,677,067 A | 10/1997 | Kojima et al. | |
| 620,725 A1 | 3/2001 | Varnell | |
| 6,207,258 B1 * | 3/2001 | Varnell ........................ | 428/32.1 |
| 6,576,326 B2 | 6/2003 | Hatano et al. | |
| 6,835,240 B2 | 12/2004 | Nishita et al. | |
| 6,880,928 B2 | 4/2005 | Hosoi et al. | |
| 6,984,033 B2 | 1/2006 | Bringley et al. | |
| 7,138,162 B2 | 11/2006 | Sharma et al. | |
| 2001/0012556 A1 * | 8/2001 | Kondo et al. ................. | 428/195 |
| 2003/0227531 A1 | 12/2003 | Hosoi et al. | |
| 2004/0046848 A1 * | 3/2004 | Payne et al. .................... | 347/101 |
| 2005/0041081 A1 * | 2/2005 | Horii et al. ..................... | 347/95 |
| 2005/0217815 A1 | 10/2005 | Stoffel et al. | |
| 2006/0228499 A1 | 10/2006 | Tran et al. | |
| 2007/0087136 A1 | 4/2007 | Stoffel et al. | |
| 2009/0274855 A1 * | 11/2009 | Koenig et al. .............. | 428/32.21 |

FOREIGN PATENT DOCUMENTS

| | | |
|---|---|---|
| EP | 0461558 | 12/1991 |
| EP | 1447237 | 8/2004 |
| JP | 07-214893 | 8/1995 |
| JP | 09-314985 | 12/1997 |
| WO | WO-2006035004 | 4/2006 |

OTHER PUBLICATIONS

Hewlett-Packard Development Company, L.P., International Search Report and Written Opinion dated Feb. 24, 2009, PCT App. No. PCT/US2008/065390, filed May 30, 2008.
Mitsubishi Paper Mills Limited, Machine Translation of JP07-214893, Aug. 15, 1995.
Extended European Search Report for European Application No. 08769918.7 mailed on Jul. 19, 2012.
Taiwanese Examination Report dated Feb. 25, 2013.

* cited by examiner

Primary Examiner — Betelhem Shewareged (57) ABSTRACT

An ink-jet recording medium is disclosed which comprises a paper substrate having a surface for receiving an ink-jet ink containing a pigmented colorant. The surface is treated with at least one co-crystalline salt, which become associated with the substrate surface. The co-crystalline salt is capable of crashing pigmented colorants on the paper surface, and its use may help protect paper manufacturing equipment from corrosion.

20 Claims, 1 Drawing Sheet

MEDIA FOR INKJET PRINTING

CROSS-REFERENCE TO RELATED APPLICATION

The present application is the U.S. national stage of international patent application number PCT/US2008/065390, filed 30 May 2008, and claims the benefit thereof under 35 U.S.C. §119(a) and 35 U.S.C. §365(a). The disclosure of that international application is hereby incorporated herein by reference.

BACKGROUND

With rapid development of digital printing technology such as thermal ink-jet printing, traditional printing papers face great challenges when used as the ink-jet print media. In addition to good image quality and low cost, print media today are generally expected to be able to dry quickly and to avoid image strike-through, especially when a sheet is printed on both sides.

The image quality, including ink optical density (OD), color gamut, and the ink drying time, which result from ink-jet printing greatly depend on the interaction of the ink and media, and especially on the ink-absorption capability of media. The ability of the paper stock to absorb aqueous solvents and the speed at which it absorbs the solvent are major considerations in the manufacturing of media for receiving ink-jet inks. For example, excessive absorption will bring the colorant into the bulk area of the base, resulting in low black and color optical density and low color gamut. This tends to create a "washed out" image. Poor absorption, on the other hand, creates a situation in which the ink bleeds and smears readily. Drying time of the ink is also increased when the paper stock has poor absorption characteristics.

Absorption of aqueous solvents by a paper stock is mainly controlled by the sizing processing of the paper stock during manufacture. This includes the processes of internal and surface sizing. The desired absorption properties of the paper stock for absorbing aqueous solvents are customarily controlled by balancing internal sizing and surface sizing.

To improve the quality of paper media printed with pigmented inks, a recently developed technology is now in use in the paper manufacturing process. This recent technology includes adding a divalent metal salt (e.g., calcium chloride), into the surface sizing composition during paper surface finishing processing. During subsequent use of the treated paper stock, when ink drops containing a pigment colorant are ejected onto the paper containing the metallic salt, the pigment "crashes out" of the pigment suspension solution. The metallic salt causes the pigmented colorant to separate from the aqueous solvent. In the case of calcium chloride salt treatment, calcium cations interact with anionic charged pigmented colorants and act as a colorant fixing agent. The salt causes the colorants to stay on the outermost surface of the print medium. In this way, the optical density of the image is increased and the ink drying time is reduced. In order to obtain satisfactory performance, a minimum amount of salt greater than 6-8 kg (salt)/T (paper) is customarily needed. However, such a high loading of chloride-containing compounds promotes drastic corrosion of the paper milling equipment used to produce the print media, and significantly reduces the life span of the salt-contacting parts of the paper manufacturing equipment, such as sizing rolls for instance.

Another drawback commonly associated with the use of calcium chloride salt arises from its exothermic dissolution in water. A significant amount of heat is produced when large batches of calcium chloride salt solution are prepared, as is customary in commercial paper manufacturing processes. Solution temperatures can easily reach 90-100° C. or more. Still another downside of using chloride salts in the manufacture of print media is that the associated chloride-containing vapors may pose health and safety issues for the operators. There is continuing interest in the development of ways to produce ink-jet print media that perform well with pigmented inks.

SUMMARY

Compositions and methods are disclosed for making and using ink-jet print media comprising co-crystalline salts. Embodiments of the print media perform well with pigmented ink-jet inks and avoid certain drawbacks of prior art print media and related manufacturing methods.

BRIEF DESCRIPTION OF THE DRAWINGS

For a detailed description of exemplary embodiments of the invention, reference will now be made to the accompanying drawings in which.

NOTATION AND NOMENCLATURE

Certain terms are used throughout the following description and claims to refer to particular system components. As one skilled in the art will appreciate, computer companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ."

The term "image quality" when referring to an ink-jet printed image, refers to some or all of the following characteristics: optical density, color gamut, line raggedness, strikethrough, and ink dry time of the printed medium.

"Color gamut" refers to the subset of colors which can be accurately represented in a given circumstance, such as within a given color space like CIE 1976 (L*, a*, b*) color space.

"Line raggedness" refers to the average of the leading edge and trailing edge raggedness of a printed line and it measures the appearance of geometric distortion of an edge from its ideal position.

"Optical density" (OD) is the measurement of the change in reflectance $OD=\log_{10}(I_i/I_r)$, where $I_i$ and $I_r$ are incident and reflected light intensities, respectively.

"Ink dry time" refers to the time it takes for the ink to dry such that it will not smear or transfer to other surfaces.

"Image strike through" refers to an image defect in which the image printed on the first side of a print media can be seen from the opposite side. It is usually caused by poor opacity of media and/or excessive ink penetration to the opposite side.

As used herein, the term "co-crystalline salt" or "double salt" refers to a salt made up of at least two different types of cations and one type of anion, or of at least two different types of anions and one type of cation. These chemicals exist in such a way as to form a new compound which is crystallographically distinct from either of the constituents (single salts).

"Crashing" or "crashes out," when referring to a pigmented ink applied to a print medium, means that stabilized suspension of pigmented colorants with aqueous solvent is disturbed and pigment particles are precipitated from suspension.

"Paper," "paper substrate," "printing media," "paper stock" or "base stock" includes traditional papers such as woody paper, non-woody paper; synthetic paper, and regenerated paper. More generally, these terms are meant to encompass a substrate based on cellulosic fibers and other known paper fibers. The substrate may be of any dimension, e.g., size or thickness, or form such as pulp, wet paper, and dry paper, for example. The substrate can be in the form of a roll and broad, or in the form of a flat or sheet structure, which may be of variable dimensions. In particular, substrate is meant to encompass plain paper or un-coated paper, writing paper, drawing paper, photobase paper, coated paper and the like. For example, the paper substrate may be from about 2 mils to about 30 mils thick, depending on a desired end application for the print medium.

The term "hardwood pulps" refers to fibrous pulp derived from the woody substance of deciduous trees (angiosperms) such as birch, oak, beech, maple, and eucalyptus.

The term "softwood pulps" refers to fibrous pulps derived from the woody substance of coniferous trees (gymnosperms) such as varieties of fir, spruce, and pine, as for example loblolly pine, slash pine, Colorado spruce, balsam fir and Douglas fir.

Temperature, ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 1-10 Kg should be interpreted to include not only the explicitly recited limits of about 1 Kg to about 10 Kg, but also to include sub-ranges such as 1 to 8 Kg, 2 to 5 Kg, and so forth, as well as individual amounts, including fractional amounts, within the specified ranges, such as 2 Kg, 3.5 Kg, and 5 Kg, for example.

The term "about" when referring to a numerical value or range is intended to encompass the values resulting from experimental error that can occur when taking measurements.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

An ink-jet ink receptive print medium includes an ink-receiving surface or layer that includes at least one co-crystalline salt compound that functions as a colorant fixative when the medium is used for ink-jet printing. The co-crystalline salt crashes out the pigmented ink colorants particles from suspended ink vehicle, and then chemically, physically, and/or electrostatically binds the pigmented colorant material in the ejected ink at or near the outer surface of the print medium, and thereby enhances overall image quality of the printed medium. Another function of co-crystalline salts is to reduce the ink's dry time.

Any suitable co-crystalline salt of an inorganic acid, organic acid, organometallic compound, or other metal complex (other than metal oxides) in which a ligand is bound to a metal ion by a chemical bond, such as a covalent bond, ionic bond, coordination covalent bond, metallic bond, aromatic bond or bent bond, is used to treat a paper surface. The co-crystalline salt must be capable of being uniformly dissolved or dispersed in a suitable liquid, such as water or other aqueous solvent, to form a surface treatment composition. Examples of suitable metal cations include, but are not limited to, potassium, sodium, lithium, aluminum, calcium, magnesium, zinc, iron, strontium, barium, nickel, copper, scandium, gallium, indium, titanium, zirconium, tin and lead. Compounds comprising magnesium, aluminum, zirconium, calcium and zinc cations are preferable in some instances, especially when a colorless composition is desired. In some instances polyvalent metal cations are preferred due to their stronger interaction with pigmented colorants in the inks. The metal cations of the co-crystalline salts play an important role in improving image quality of a printed image.

Examples of suitable multi-cation co-crystalline salts include, but are not limited to, potassium sodium tartrate, potassium sodium bromlite; potassium dihydrogen citrate; lithium potassium hydrogen citrate monohydrate; tamarugite $(NaAl(SO_4)_x \cdot 6H_2O)$, barium silicon iodide $(Ba_3SiI_2)$; potassium tetrachloroaluminate $(AlKCl_4)$; lithium tetrachloroaluminate $(AlLiCl_4)$; sodium tetrachloroaluminate $(AlNaCl_4)$; cesium tetrachloroaluminate $(AlCeCl_4)$; aluminum hexafluoroaluminate; potassium aluminum sulfate dodecahydrate; potassium tetrafluoroborate $(BF_4K)$; lithium tetrafluoroborate; sodium tetrafluoroborate; calcium tetrafluoroborate hydrate $(B_2CaF_8)$; tin tetrafluoroborate $(B_2SnF_8)$; titanium chloride-aluminum chloride $(AlCl_{12}Ti_3)$; aluminum cesium sulfate dodecahydrate $(AlCsO_8S_2 \cdot 12H_2O)$; magnesium aluminum hydrotalcites, and calcium magnesium acetate (sometimes referred to herein as "CMA").

Co-crystalline salts of alkali sulfates represent another major group of multi-cation co-crystalline salts. These salts can be written as the general formula $$M^+{}_2SO_4 \cdot M^{3+}{}_2(SO_4)_3 \cdot 24H_2O,$$

wherein $M^+$ denotes an alkali metal (e.g., lithium, sodium, potassium, rubidium, or cesium) or ammonium ion $(NH^{4+})$, and $M^{3+}$ denotes one of the trivalent metal ions (e.g., aluminum, chromium, or iron (III)).

Some multi-anion co-crystalline salts are also suitable for use in preparing a paper surface treatment composition. They include, but are not limited to, zinc chloride co-crystalline salts such as 4-phenoxydiazobenzene zinc chloride and 2,5-dimethoxy-4-tolylmercaptodiazobenzene zinc chloride; magnesium nitrate co-crystalline salts such as triacetatohexaaquodimagnesium nitrate; calcium salts of organic acids with different combinations of acid anions, such as those represented by the general structure Ca—R1—R2 wherein R1 and R2 are different from each other, but both have the general structure —OOC—R3, wherein R3 is a saturated or monounsaturated or polyunsaturated C1-C5, C1-C5 hydroxyakyl or phenyl.

The desired co-crystalline salt is applied to the print media during manufacture, as described in more detail below.

The paper base or substrate used to make an ink-jet paper comprises any suitable type of cellulose fiber, or combination of fibers known for use in paper making. For example, the substrate can be made from pulp fibers derived from hardwood trees, softwood trees, or a combination of hardwood and softwood trees prepared for use in papermaking fiber obtained by known digestion, refining, and bleaching operations, such as those that are customarily employed in mechanical, thermomechanical, chemical and semi-chemical, pulping or other well-known pulping processes. For some applications, all or a portion of the pulp fibers are obtained from non-woody herbaceous plants such as kenaf, hemp, jute, flax, sisal and abaca, for example. Either bleached or unbleached pulp fiber may be utilized in preparing a suitable paper base for the print media. Recycled pulp fibers are also suitable for use. In certain applications, the paper base is made by combining 30% to about 100% by weight hardwood fibers and from about 0% to about 70% by weight softwood fibers.

Additionally, any of a number of fillers may be included in various amounts in the paper pulp during formation of the substrate, to control physical properties of the final substrate, depending upon the particular requirements of the user. Some suitable fillers are ground calcium carbonate, precipitated calcium carbonate, titanium dioxide, kaolin clay, and silicates, to name just a few, may be incorporated into a pulp. For instance, for many paper base formulations the filler content of the pulp is in the range of about 0% to about 40% by weight of the dry fiber pulp. In some of those applications the filler represents about 10% to about 20% by weight of the dry fiber pulp.

An exemplary inkjet printing media comprises a base stock such as a cellulose paper and a surface treatment composition applied on a single side or on both sides of the base stock. The cellulose base paper has a basis weight ranging from about 35-250 gsm, with about 5 to 35% by weight of filler. The base paper contains wood pulp such as groundwood pulp, thermomechanical pulp and chemo-thermomechanical pulp, and additionally or alternatively, contains wood-free pulp.

Internal Sizing of Paper Stock. For most applications at least one sizing agent is added to the pulp suspension before it is converted to a paper web or substrate, to provide internal sizing of the substrate (also referred to as the paper stock). This internal sizing treatment helps to develop in the resulting substrate a resistance to liquids during use. During further stages of the paper making processing, the internal sizing also prevents any subsequently-applied surface sizing from soaking into the finished sheet, thereby allowing the surface sizing to remain on the surface where it has maximum effectiveness. Internal sizing agents that are suitably used for this purpose include any of those commonly used at the wet end of a paper manufacturing machine. For example, rosin; rosin precipitated with alum ($Al_2(SO_4)_3$); abietic acid and abietic acid homologues such as neoabietic acid and levopimaric acid; stearic acid and stearic acid derivatives; ammonium zirconium carbonate; silicone and silicone-containing compounds; fluorochemicals of the general structure $CF_3(CF_2)_n$R, wherein R is anionic, cationic or another functional group; starch and starch derivatives; methyl cellulose; carboxymethylcellulose (CMC); polyvinyl alcohol; alginates; waxes; wax emulsions; alkylketene dimmer (AKD); alkenyl ketene dimer emulsion (AnKD); alkyl succinic anhydride (ASA); emulsions of ASA or AKD with cationic starch; ASA incorporating alum; and other known internal sizing agents and combinations of those. The internal sizing agents are generally used at concentration levels known to those who practice the art of paper making. For instance, in some applications the amount of internal sizing agent is in the range of about 0.3 kg IT of base paper stock to 20 kg/T.

Surface Sizing of Paper Stock. A surface sizing composition is applied to the paper stock (substrate) as a surface treatment to aid in the development of resistance to penetration of liquids through the paper, and also to improve paper surface smoothness. Some suitable surface sizing agents are starches and starch derivatives; carboxymethylcellulose (CMC); methyl cellulose; alginates; waxes; wax emulsions; alkylketene dimer (AKD); alkyl succinic anhydride (ASA); alkenyl ketene dimer emulsion (AnKD); emulsions of ASA or AKD with cationic starch; ASA incorporating alum; water-soluble polymeric materials, such as polyvinyl alcohol, gelatin, acrylamide polymers, acrylic polymers or copolymers, vinyl acetate latex, polyesters, vinylidene chloride latex, styrene-butadiene, acrylonitrile-butadiene copolymers, styrene acrylic copolymers and copolymers, and various combinations of those agents. In many applications some type of starch is used as the surface sizing agent. Examples of suitable starches are corn starch, tapioca starch, wheat starch, rice starch, sago starch and potato starch. These starch species may be unmodified starch, enzyme modified starch, thermal and thermal-chemical modified starch and chemical modified starch. Examples of chemical modified starch are converted starches such as acid fluidity starches, oxidized starches and pyrodextrins; derivatized starches such as hydroxyalkylated starches, cyanoethylated starch, cationic starch ethers, anionic starches, starch esters, starch grafts, and hydrophobic starches. The surface sizing agents are generally used at concentration levels customary in the art of paper making. In some instances, the surface sizing agent contains both starch and a synthetic sizing agent. For example, the pick-up amount of starch is 0.5-6 grams per square meter (gsm)/paper side, and the amount of synthetic surface sizing agent is in the range of 0-6 kg/T.

At the same time that the surface sizing is applied, the substrate surface may also be treated with one or more co-crystalline salt compounds, as described above. For some applications, the co-crystalline salt is mixed into the surface sizing solution together with sizing agents like starch, and applied simultaneously with starch on the surface of paper web. Accordingly, in some instances a surface treatment composition comprises at least one surface sizing agent and at least one co-crystalline salt compound. For other applications, the co-crystalline salt is applied on the web surface first and followed by a surface sizing agent (e.g., starch). For still other applications, the sizing agent (e.g., starch) is first pressed on the web surface and then the co-crystalline salt is applied on top of the starch. The co-crystalline salt is applied in the solid form (e.g., dispersed with aqueous starch solution) or in liquid form by re-dissolving into water, if the salt is water soluble. In the latter case, a stronger action between cations and pigments is possible, and, therefore, in some embodiments, is potentially more effective in crashing the ink pigments.

Both internal sizing and surface sizing controls the paper's absorption capacity and absorption speed with respect to applied inks. The degree of sizing is determined primarily by the type and amount of sizing agents used for a particular application. The absorption of aqueous solvents may be characterized by Cobb size values and Bristow Wheel absorption rate, for example. To obtain an optimum result, the Cobb value typically ranges from 20 to 50 gsm in 60 seconds, preferably in the range of about 25-35 gsm. Absorption rate as measured by Bristow Wheel Dynamic Sorption Tester ranges from 5 ml/m$^2$/second to 50 ml/m$^2$/second, with a wheel speed of 1.25 mm/sec.

A surface treatment composition including a surface sizing agent and one or more above-described co-crystalline salts, in the form of a solution or dispersion, is applied to the base paper stock by any suitable surface size press process such as a puddle-size press and film-size press, or the like, as are known in the art of paper manufacturing. The puddle-size press may be configured as having horizontal, vertical, or inclined rollers. The film-size press may include a metering system, such as gateroll metering, blade metering, Meyer rod metering, or slot metering. In some embodiments, a film-size press with short-dwell blade metering is used as an application head to apply the surface treatment composition. In embodiments, the applied weight of surface treatment composition is controlled in the range of 0.5-6 gsm (grams per square meter) per side of paper stock. Of that total amount, the applied weight of co-crystalline salt ranges from about 0.02 to about 1.8 gsm, and in some cases is about 0.05 to about 0.6 gsm. A calendaring process may optionally be used after drying the surface treatment composition to improve surface smoothness and gloss. In embodiments, the resulting print medium comprises a treated surface coat weight in the range of about 1 to 8 Kg of co-crystalline salt per ton of dry paper, and in some cases the coatweight is in the range of about 2.5 to about 3 Kg/T.

In some embodiments it may be desirable to apply the surface sizing agent and the co-crystalline salt composition separately instead of applying them together in a single surface treatment composition as described above. In such instances, a co-crystalline salt composition and a composition containing the surface sizing agent (e.g., starch) are sequentially applied to the fiber web as described above, with or without drying of the fiber web (paper stock) between applications.

Embodiments of the resulting surface treated print media provide very good printing quality when used with pigmented inks. In embodiments, the print media show excellent performance comparable to or better than conventional $CaCl_2$-containing systems, and at the same time provide lower risk for corrosion of paper manufacturing equipment and are less exothermic during manufacture and application of the surface treatment composition.

In some embodiments, CMA is advantageously used as a replacement for some or all of a $CaCl_2$ surface treatment composition. CMA is non-corrosive and biodegradable, and offers the potential advantage of avoiding the paper mill equipment corrosion problems associated with use of chloride salts during manufacture of print media. Another potential advantage of using a CMA colorant fixative is the low exothermal potential which may improve or eliminate the high temperature concerns that commonly occur with salt mixing in paper mills. Although the unit price of CMA is generally higher than conventional salts such as NaCl and $CaCl_2$, in some instances it will nevertheless be cost effective to deter corrosion of paper manufacturing equipment by partially or entirely replacing commonly used lower cost salts such as NaCl and $CaCl_2$ with CMA, or another co-crystalline salt. Embodiments of CMA-containing print media also offer potential for more rapid ink dry times compared to NaCl or $CaCl_2$-containing print media.

The resulting treated printing media are suitably employed with any ink-jet printer using pigmented inks for any drop on demand or continuous ink jet technology, such as thermal ink-jet or piezoelectric ink-jet technology. Pigmented ink-jet inks are well known in the art, and typically contain a liquid vehicle, pigment colorants, and additional components including one or more dyes, humectants, detergents, polymers, buffers, preservatives, and other components. A pigment or any number of pigment blends may be provided in the ink-jet ink formulation to impart color to the resulting ink. The pigment may be any number of desired pigments dispersed throughout the resulting ink-jet ink. More particularly, the pigment included in the present inkjet ink may include, but is in no way limited to, self-dispersed (surface modified) pigments, or pigments accompanied by a dispersant, as discussed in more detail below.

The pigmented ink-jet inks that are used with an above-described co-crystalline salt treated paper substrate may contain any suitable organic or inorganic pigment particles, including black pigments, white pigments, cyan pigments, magenta pigments, yellow pigments, and the like. Examples of suitable inorganic pigments are titanium oxide, cobalt blue ($CoO$—$Al_2O_3$), chrome yellow ($PbCrO_4$), and iron oxide. Suitable organic pigments include, for example, carbon black, azo pigments including diazo pigments and monoazo pigments, polycyclic pigments (e.g., phthalocyanine pigments such as phthalocyanine blues and phthalocyanine greens, perylene pigments, perynone pigments, anthraquinone pigments, quinacridone pigments, dioxazine pigments, thioindigo pigments, isoindolinone pigments, pyranthrone pigments, and quinophthalone pigments), insoluble dye chelates (e.g., basic dye type chelates and acidic dye type chelate), nitropigments, nitroso pigments, anthanthrone pigments such as PR168, and the like. Representative examples of phthalocyanine blues and greens include copper phthalocyanine blue, copper phthalocyanine green and derivatives thereof (Pigment Blue 15 and Pigment Green 36). Representative examples of quinacridones include Pigment Orange 48, Pigment Orange 49, Pigment Red 122, Pigment Red 192, Pigment Red 202, Pigment Red 206, Pigment Red 207, Pigment Red 209, Pigment Violet 19 and Pigment Violet 42. Representative examples of anthraquinones include Pigment Red 43, Pigment Red 194 (Perinone Red), Pigment Red 177, Pigment Red 216 (Brominated Pyranthrone Red) and Pigment Red 226 (Pyranthrone Red). Representative examples of perylenes include Pigment Red 123 (Vermillion), Pigment Red 149 (Scarlet), Pigment Red 179 (Maroon), Pigment Red 190 (Red), Pigment Red 189 (Yellow Shade Red) and Pigment Red 224. Representative examples of thioindigoids include Pigment Red 86, Pigment Red 87, Pigment Red 88, Pigment Red 181, Pigment Red 198, Pigment Violet 36, and Pigment Violet 38. Representative examples of heterocyclic yellows include Pigment Yellow 1, Pigment Yellow 3, Pigment Yellow 12, Pigment Yellow 13, Pigment Yellow 14, Pigment Yellow 17, Pigment Yellow 65, Pigment Yellow 73, Pigment Yellow 74, Pigment Yellow 90, Pigment Yellow 110, Pigment Yellow 117, Pigment Yellow 120, Pigment Yellow 128, Pigment Yellow 138, Pigment Yellow 150, Pigment Yellow 151, Pigment Yellow 155, and Pigment Yellow 213. Such pigments are commercially available in either powder or press cake form from a number of sources including, BASF Corporation, Engelhard Corporation and Sun Chemical Corporation.

Examples of suitable black pigments are carbon black, graphite, vitreous carbon, charcoal, and combinations thereof. Such carbon pigments can be manufactured by a variety of known methods such as a channel method, a contact method, a furnace method, an acetylene method, or a thermal method, and are commercially available from such vendors as Cabot Corporation, Columbian Chemicals Company, Degussa AG, and E.I. DuPont de Nemours and Company. Suitable carbon black pigments include, but are not limited to, Cabot pigments such as MONARCH 1400, MONARCH 1300, MONARCH 1100, MONARCH 1000, MONARCH 900, MONARCH 880, MONARCH 800, MONARCH 700, CAB-O-JET 200, CAB-O-JET 300, REGAL, BLACK PEARLS, ELFTEX, MOGUL, and VULCAN pigments; Columbian pigments such as RAVEN 7000, RAVEN 5750, RAVEN 5250, RAVEN 5000, and RAVEN 3500; Degussa pigments such as Color Black FW 200, RAVEN FW 2, RAVEN FW 2V, RAVEN FW 1, RAVEN FW 18, RAVEN S160, RAVEN FW S170, Special Black 6, Special Black 5, Special Black 4A, Special Black 4, PRINTEX U, PRINTEX 140U, PRINTEX V, and PRINTEX 140V; and TIPURE R-101 available from Dupont. The above list of pigments includes unmodified pigment particulates, small molecule attached pigment particulates, and polymer-dispersed pigment particulates. Alternatively, almost any commercially available carbon pigment may be used, as long as it provides acceptable optical density and print characteristics.

Similarly, a wide variety of colored pigments can be used in ink-jet inks that are usable with the co-crystalline salt-treated paper media, and can be blue, brown, cyan, green, white, violet, magenta, red, orange, yellow, and mixtures thereof. Non limiting examples of suitable color pigments are CABO-JET 250C, CABO-JET 260M, and CABO-JET 270Y (Cabot Corp.); PALIOGEN Orange, PALIOGEN Orange 3040, PALIOGEN Blue L 6470, PALIOGEN Violet 5100, PALIOGEN Violet 5890, PALIOGEN Yellow 1520, PALIOGEN Yellow 1560, PALIOGEN Red 3871K, PALIOGEN Red 3340, HELIOGEN Blue L 6901F, HELIOGEN Blue NBD 7010, HELIOGEN Blue K 7090, HELIOGEN Blue L 7101 F, HELIOGEN Blue L6900, L7020, HELIOGEN Blue D6840, HELIOGEN Blue D7080, HELIOGEN Green L8730, HELIOGEN Green K 8683, and HELIOGEN Green L 9140 (BASF Corp); CHROMOPHTAL Yellow 3G, CHROMOPHTAL Yellow GR, CHROMOPHTAL Yellow 8G, IGRAZIN Yellow 5GT, IGRALITE Rubine 4BL, IGRALITE Blue BCA, MONASTRAL Magenta, MONASTRAL Scarlet, MONASTRAL Violet R, MONASTRAL Red B, and MONASTRAL Violet Maroon B (Ciba-Geigy Corp.); DALAMAR Yellow YT-858-D and HEUCOPHTHAL Blue G XBT-583D (Heubach Group); Permanent Yellow GR, Permanent Yellow G, Permanent Yellow DHG, Permanent Yellow NCG-71, Permanent Yellow GG, Hansa Yellow RA, Hansa Brilliant Yellow 5GX-02, Hansa Yellow-X, NOVOPERM Yellow HR, NOVOPERM Yellow FGL, Hansa Brilliant Yellow 10GX, Permanent Yellow G3R-01, HOSTAPERM Yellow H4G, HOSTAPERM Yellow H3G, HOSTAPERM Orange GR, HOSTAPERM Scarlet GO, HOSTAPERM Pink E, Permanent Rubine F6B, and the HOSTAFINE series (Hoechst Specialty Chemicals); QUINDO Magenta, INDOFAST Brilliant Scarlet, QUINDO Red R6700, QUINDO Red R6713, and INDOFAST Violet (Mobay Corp.); L74-1357 Yellow, L75-1331 Yellow, and L75-2577 Yellow (Sun Chemical Corp.). Other examples of color pigments for ink-jet inks are Normandy Magenta RD-2400, Permanent Violet VT2645, Argyle Green XP-111-S, Brilliant Green Toner GR 0991, Sudan Blue OS, PV Fast Blue B2GO1, Sudan III, Sudan II, Sudan IV, Sudan Orange G, Sudan Orange 220, Ortho Orange OR2673, Lithol Fast Yellow 0991K, Paliotol Yellow 1840, Lumogen Yellow D0790, Suco-Gelb L1250, Suco-Yellow D1355, Fanal Pink D4830, Cinquasia Magenta, Lithol Scarlet D3700, Toluidine Red, Scarlet for Thermoplast NSD PS PA, E. D. Toluidine Red, Lithol Rubine Toner, Lithol Scarlet 4440, Bon Red C, Royal Brilliant Red RD-8192, Oracet Pink RF, and Lithol Fast Scarlet L4300 (available, variously, from known commercial sources such as Hoechst Celanese Corporation, Paul Uhlich, BASF, American Hoechst, Ciba-Geigy, Aldrich, DuPont, Ugine Kuhlman of Canada, Dominion Color Company, Magruder, and Matheson).

The ink-jet inks used with the co-crystalline salt-treated paper print media may contain one or more distinct type of pigment. In many embodiments, the mass average diameter of the pigment particles is about 10 nm to about 10 µm, and in some cases the average diameter is in the range of about 10 nm to about 500 nm, although sizes outside these ranges may also be used if the selected pigment can remain dispersed in the ink composition and the pigment particles provide adequate color properties. In some embodiments the pigment comprises an amount in the range of about 1% to about 20% by weight of the ink-jet ink composition, and in certain cases comprises an amount in the range of about 2% to about 6% by weight of the ink-jet ink composition.

The pigment colorants may include one or more attached dispersant. Dispersants may help to improve dispersion stability, and may also serve to improve bleed control of the ink on the print media. Examples of suitable dispersant include, but are not limited to, a carboxylic acid, or a reactive group such as alcohol, amine, anhydride, sulfonic acid, thiol, halotriazine, maleimide, vinyl sulfone, or the like. A wide variety of dispersants for pigmented ink-jet inks are known in the art. Such dispersants are broadly classed as polyalkyl glycols, polyalkyl imines, aryl dicarboxylic acids such as phthalic acids, isophthalic acids, terephthalic acids, carbohydrates, acrylates, methacrylates, trehalose, and isomers thereof. Generally, the glycol dispersants tend to be stable at neutral and higher pH, while imine dispersants tend to be stable at lower pH (e.g., about pH 4-6). In some applications, a polyethylene glycol dispersant is attached to the pigment particles in the ink. Examples of some suitable dispersants include, but are not limited to, polypropylene glycol, polyethylene imine, polyethylene glycol, trehalose, and combinations thereof. In some embodiments, the pigment also has a polymer coupled thereto, the polymer being additionally coupled to a dispersant, such that the pigment is polymer-dispersed.

The pigmented ink-jet inks suitable for use with the surface treated print media described herein may additionally include any suitable vehicles or additives as are known in the art of preparing ink-jet inks. Some of these include water, organic co-solvents, dye-based colorants, pH buffers, viscosity modifiers, antimicrobials, and surfactants.

The ink drying time of the resulting ink-jet printed medium (ink dry time) is the time it takes for the deposited ink to dry out such that it will not smear or transfer to other surfaces. The dry time is determined by the amount of ink transferred from a printed to an unprinted portion of the media sheet after rolling with a roller of fixed weight. The ink transfer is defined as the amount of optical density transferred after rolling with a roller, and is expressed as a percentage of the optical density transferred to the unprinted portion of the recording sheet after rolling with a roller. The method involves printing solid colored blocks on paper, waiting for a fixed amount of time, 5 seconds after printing, and then folding in half so that the printed portion contacts an unprinted portion of the recording sheet, and rolling with a 4.5 lb hand roller. In exemplary test results, the percentage of ink transferred on the control printing media (containing no co-crystalline salt) has the ink transferring in the range of 15-30%, while the transferring is reduced to 2-10% with use of ink-jet inks containing a co-crystalline salt.

EXAMPLE 1

A series of ink-jet printing media were prepared using the following procedure:

(A) The paper substrates used in this experiment were made on a paper machine from a fiber furnish consisting of 30% softwood and 50% hardwood fibers and 12% precipitated calcium carbonate with alkenyl succinic anhydride (ASA) internal size. The basis weight of the substrate paper was about 75 gsm.

(B) The surface sizing composition was prepared in the laboratory using a 55 gal jacked processing vassal made by stainless steel (A&B Processing System Corp., Stratford, Wis.). A Lighthin mixer (Lighthin Ltd, Rochester N.Y.) mixer with gear ratio 5:1 and a speed of 1500 rpm is used to mix the formulation. The cationic starch was first pre-cooked at 95° C. for 2 hrs and cooled to room temperature. An amount of pre-cooked starch was added to the mixing container, then the water, and then the other additives such as fluorescent whitening agents (FWA) and pH buffer. The water soluble co-crystalline salt CMA was pre-dissolved and filtered, and then mixed with starch mixture at 500-1000 rpm.

An exemplary formulation of the surface treatment composition may include (as a non-limiting example):
 Cationic Starch: 15-100 kg/T of paper substrate;
 Calcium Magnesium Acetate (CMA): 1-10 kg/T of paper substrate;
 Fluorescent whitening agents (FWA): about 0.5-12 kg/T of paper substrate; and
 Synthetic surface sizing agent: 0-5 kg/T of paper substrate.

(C) Size press treated ink-jet media was prepared by applying the resulting surface sizing composition either by hand drawdown using a Mayer rod, or a continuous lab coater. By controlling the formulation solids, rod size or nip pressure, and machine running speed, a pickup weight of about 0.5 to 2.0 gsm per side was achieved. The treated sheets were dried in a hot air oven. Print media samples containing 0.25, 1.5, 2.4, 4.6, 6.5, 8.3 and 10 Kg/T CMA were prepared.

EXAMPLE 2

Figure 1:
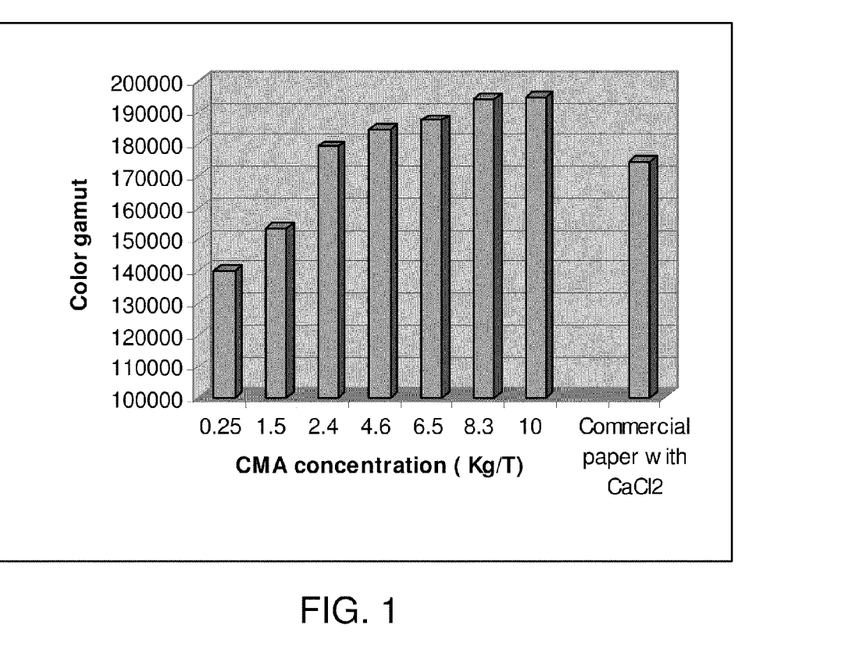
FIG. 1 is a bar graph showing comparative color gamut measurements of certain print media samples containing co-crystalline salts, in accordance with embodiments of the invention.

The print media samples prepared as described in Example 1 were tested in order to show the differences in terms of color gamut and line raggedness between samples with different co-crystalline salt loading. The samples were printed using HP PhotoSmart Pro B9180 with pigmented black and color inks, manufactured by Hewlett-Packard Co. The color gamut of each printed image was recorded, and the results are provided as a bar graph in FIG. 1, with the y axis gauging increasing amounts of C L*a*b* volume, a measure of color gamut. The color gamut measurements were carried out on squares of primary color (cyan, magenta, and yellow) and secondary colors (red, green, and blue) plus white (un-imaged sheets) and black colors. L*a*b* values were obtained from the measurement and thereafter were used to calculate the 8-point color gamut, where the higher value of color gamut indicates that the prints showed richer or more saturated colors. As shown in FIG. 1, the color gamut measurements showed increase in terms of color gamut in the samples with CMA. When CMA usage was over 2.0-3.0 Kg/T of dry base paper, the color gamut achieved a value comparable to that of a commercial inkjet printing paper which contains 5-8 kg/T of $CaCl_2$.

Figure 2:
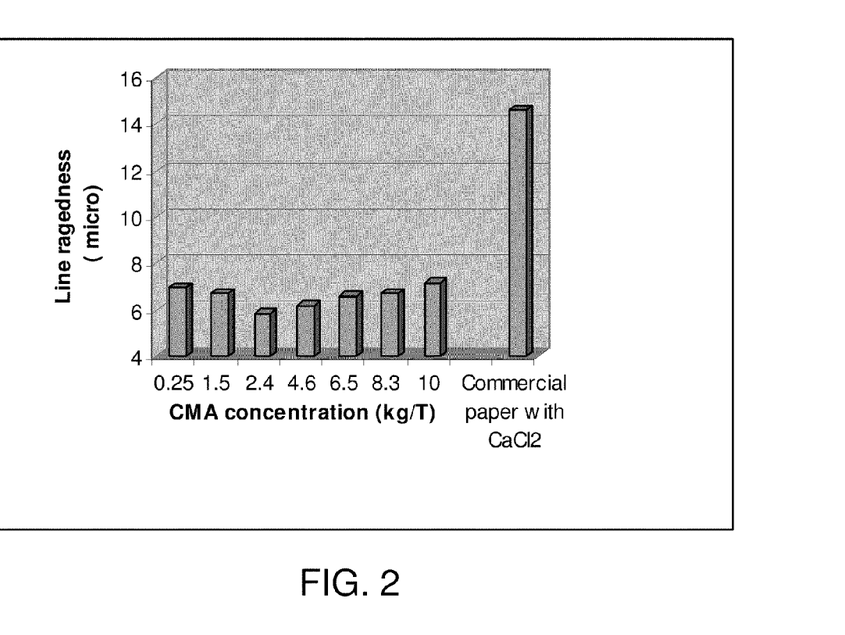
FIG. 2 is a bar graph showing comparative line raggedness measurements of printed media samples containing co-crystalline salts, in accordance with embodiments of the invention.

Line raggedness is the average of the leading edge and trailing edge raggedness and measures the appearance of geometric distortion of an edge from its ideal position. In this evaluation, media samples were imaged as black lines on yellow background with a HP DJ6940 Color Inkjet Printer, manufactured by Hewlett-Packard Co. The samples were then allowed to air dry. The edge acuity of the black-to-yellow bleed was measured with a QEA Personal Image Analysis System (Quality Engineering Associates, Burlington, Mass.). Smaller values are indicative of better edge quality of the printed image. In the bar graph shown in FIG. 2, the y axis gauges increasing amounts of line raggedness as measured in microns. The samples containing different loadings of CMA clearly show less line raggedness (lower line raggedness value) than the commercial paper contained $CaCl_2$. This result implies that media containing with co-crystalline salt will produce a print-out of a crisp image.

EXAMPLE 3

In tests like those described in Examples 1 and 2, a single cation salt ($CaCl_2$) was added to the CMA composition used to treat the paper substrate. It was surprisingly discovered that the addition of the single cation salt does not simply supplement the effects of the CMA salt, but instead acts in a synergistic way to significantly enhance the effectiveness of CMA for crashing pigment and for improving the quality of the resulting printed image. These tests showed, for example, that when only 0.5 kg/T of $CaCl_2$ was added to 1.46 kg/T of CMA, the gamut of the paper sheet made with such a mixed salts system achieved 190000 units. In other tests, the combination of 0.5 kg/T of CMA and 1.5-1.9 kg/T of $CaCl_2$ also achieved the 190000 gamut level, which is comparable to that of the commercial product which contains 4.5-7 kg/T $CaCl_2$. Advantageously, the potential corrosive effects of paper manufacturing equipment exposed to the CMA-containing surface treatment composition is potentially reduced compared to treatment with $CaCl_2$ alone.

EXAMPLE 4

In the examples 1-3, the ink dry time, which is the time period that ink dries out such that it will not smear or transfer to other surfaces, was significantly reduced under 2-6 kg/T of co-crystalline salt or co-crystalline salt/single cation salt mixture. For example, the percentage of ink transferred on the printing media containing no co-crystalline salt demonstrates an ink transfer in the range of 15-30%. This level of ink transfer is reduced to 2-10% after use of co-crystalline salt or a mixture of co-crystalline salt with $CaCl_2$ or NaCl.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An ink-jet medium comprising:
 a paper substrate having a surface treated with an alkali sulfate co-crystalline salt in combination with a co-crystalline salt selected from the group consisting of multi-cation co-crystalline salts and multi-anion co-crystalline salts.

2. The ink-jet medium of claim 1 wherein said surface is further treated with at least one sizing agent.

3. The ink-jet medium of claim 1 wherein said multi-cation co-crystalline salts comprise at least one metal cation selected from the group consisting of potassium, sodium, lithium,. aluminum, calcium, magnesium, zinc, iron, strontium, barium, nickel, copper, scandium, gallium, indium, titanium, zirconium, tin and lead.

4. The ink-jet medium of claim 1 wherein said multi-cation co-crystalline salt is selected from the group consisting of potassium sodium tartrate, potassium sodium bromite; potassium dihydrogen citrate; lithium potassium hydrogen citrate monohydrate; tamarugite ($NaAl(SO_4)_x 6H_2O$), barium silicon iodide (Ba₃SiI₂); potassium tetrachloaluminate (AlKCl₄); lithium tetrachloroaluminate (AlLiCl₄); sodium tetrachloroaluminate (AlNaCl₄); cesium tetrachloroaluminate (AlCeCl₄); aluminum hexafluoroaluminate; potassium aluminum sulfate dodecahydrate; potassium tetrafluorobotate (BF₄K); lithium tetrafluorobotate; sodium tetrafluorobotate; calcium tetrafluoroborate hydrate (B₂CaF₈); tin tetrafluoroborate (B₂SnF₈); titanium chloride-aluminum chloride (AlCl₁₂Ti₃); aluminum cesium sulfate dodecahydrate (AlCsO₈S₂.12H₂O); magnesium aluminum hydrotalcites, and calcium magnesium acetate.

5. The ink-jet medium of claim 4 wherein said multi-cation co-crystalline salt is calcium magnesium acetate.

6. The ink-jet medium of claim 1 wherein said alkali sulfate co-crystalline salt is selected from the group having the general formula $$M^+_2SO_4 \cdot M^{3+}_2(SO_4)_3 \cdot 24H_2O,$$

wherein $M^+$ denotes an alkali metal or ammonium ion (NH⁴⁺), and $M^{3+}$ denotes a trivalent metal ion.

7. The ink-jet medium of claim 6 wherein said alkali metal is selected from the group consisting of lithium, sodium, potassium, rubidium and cesium.

8. The ink-jet medium of claim 1 wherein said multi-anion co-crystalline salt is selected from the group consisting of zinc chloride co-crystalline salts, magnesium nitrate co-crystalline salts and calcium salts of organic acids having the general formula $$Ca—R1—R2$$

wherein R1 and R2 are different from each other and have the general structure —OOC—R3, wherein R3 is a saturated or monounsaturated or polyunsaturated C1-C5 alkyl, C1-C5 hydroxyakyl or phenyl group.

9. The ink-jet medium of claim 8 wherein said zinc chloride co-crystalline salt is 4-phenoxydiazobenzene zinc chloride or 2,5-dimethoxy-4-tolylmercapto-diazobenzene zinc chloride.

10. The ink-jet medium of claim 8 wherein said magnesium nitrate co-crystalline salt is triacetatohexaaquodimagnesium nitrate.

11. The ink-jet medium of claim 1 wherein said treated surface comprises 1-8 Kg of the alkali sulfate co-crystalline salt per ton of dry paper.

12. A medium comprising:
a paper substrate having a surface treated with a multi-anion co-crystalline salt,
wherein said multi-anion co-crystalline salt is selected from the group consisting of calcium salts of organic acids having the general formula $$Ca—R1—R2$$

wherein R1 and R2 are different from each other and have the general structure —OOC—R3, wherein R3 is a saturated or monounsaturated or polyunsaturated C1-C5 alkyl, C1-C5 hydroxyakyl or phenyl group.

13. The medium of claim 12, wherein said multi-anion co-crystalline salt wherein said multi-anion co-crystalline salt is selected from the group consisting of 4-phenoxydiazobenzene zinc chloride and 2,5-dimethoxy-4-tolylmercapto-diazobenzene zinc chloride.

14. The medium of claim 12, wherein said multi-anion co-crystalline salt is triacetatohexaaquodimagnesium nitrate.

15. The medium of claim 12 wherein the surface is treated with a co-crystalline salt selected from the group consisting of multi-cation co-crystalline salts and alkali surface co-crystalline salts used in combination with the multi-anion co-crystalline salt.

16. A medium, comprising:
a paper substrate having a surface treated with a multi-cation co-crystalline salt in combination with an alkali sulfate co-crystalline salt.

17. The medium of claim 16, wherein the multi-cation co-crystalline salt is selected from the group consisting of potassium sodium tartrate, potassium sodium bromite; potassium dihydrogen citrate; lithium potassium hydrogen citrate monohydrate; tamarugite (NaAl(SO₄)ₓ6H₂O), barium silicon iodide (Ba₃SiI₂); potassium tetrachloaluminate (AlKCl₄); lithium tetrachloroaluminate (AlLiCl₄); sodium tetrachloroaluminate (AlNaCl₄); cesium tetrachloroaluminate (AlCeCl₄); aluminum hexafluoroaluminate; potassium aluminum sulfate dodecahydrate; potassium tetrafluorobotate (BF₄K); lithium tetrafluorobotate; sodium tetrafluorobotate; calcium tetrafluoroborate hydrate (B₂CaF₈); tin tetrafluoroborate (B₂SnF₈); titanium chloride-aluminum chloride (AlCl₁₂Ti₃); aluminum cesium sulfate dodecahydrate (AlCsO₈S₂.12H₂O); magnesium aluminum hydrotalcites; and calcium magnesium acetate.

18. The medium of claim 16, wherein said alkali sulfate co-crystalline salt is selected from the group having the general formula $$M^+_2SO_4 \cdot M^{3+}_2(SO_4)_3 \cdot 24H_2O,$$

wherein $M^+$ denotes an alkali metal or ammonium ion (NH⁴⁺), and $M^{3+}$ denotes a trivalent metal ion.

19. The medium of claim 16, wherein said treated surface comprises 1-8 Kg of the alkali sulfate co-crystalline salt per ton of dry paper.

20. The medium of claim 16, wherein said multi-cation co-crystalline salt comprises at least one metal cation selected from the group consisting of potassium, sodium, lithium, aluminum, calcium, magnesium, zinc, iron, strontium, barium, nickel, copper, scandium, gallium, indium, titanium, zirconium, tin and lead.

* * * * *

UNITED STATES PATENT AND TRADEMARK OFFICE
CERTIFICATE OF CORRECTION

PATENT NO. : 8,507,054 B2
APPLICATION NO. : 12/995315
DATED : August 13, 2013
INVENTOR(S) : Xiaoqi Zhou et al.

Page 1 of 2

It is certified that error appears in the above-identified patent and that said Letters Patent is hereby corrected as shown below:

In the Claims

In column 12, line 59, in Claim 3, delete "lithium,." and insert -- lithium, --, therefor.

In column 13, line 1, in Claim 4, delete "tetrachloaluminate" and insert -- tetrachloroaluminate --, therefor.

In column 13, lines 5-6, in Claim 4, delete "tetrafluorobotate" and insert -- tetrafluoroborate --, therefor.

In column 13, line 6, in Claim 4, delete "tetrafluorobotate;" and insert -- tetrafluoroborate; --, therefor.

In column 13, lines 6-7, in Claim 4, delete "tetrafluorobotate;" and insert -- tetrafluoroborate; --, therefor.

In column 13, line 18, in Claim 6, delete "or" and insert -- or an --, therefor.

In column 13, line 32, in Claim 8, delete "monounsaturated or polyunsaturated" and insert -- monosaturated or polysaturated --, therefor.

In column 13, line 33, in Claim 8, delete "hydroxyakyl" and insert -- hydroxyalkyl --, therefor.

In column 14, line 1, in Claim 12, delete "monounsaturated or polyunsaturated" and insert -- monosaturated or polysaturated --, therefor.

In column 14, line 2, in Claim 12, delete "hydroxyakyl" and insert -- hydroxyalkyl --, therefor.

In column 14, line 24, in Claim 17, delete "tetrachloaluminate" and insert -- tetrachloroaluminate --, therefor.

Signed and Sealed this
Twenty-fourth Day of December, 2013

Margaret A. Focarino
*Commissioner for Patents of the United States Patent and Trademark Office*

CERTIFICATE OF CORRECTION (continued)
U.S. Pat. No. 8,507,054 B2

In column 14, lines 28-29, in Claim 17, delete "tetrafluorobotate" and insert -- tetrafluoroborate --, therefor.

In column 14, line 29, in Claim 17, delete "tetrafluorobotate;" and insert -- tetrafluoroborate; --, therefor.

In column 14, lines 29-30, in Claim 17, delete "tetrafluorobotate;" and insert -- tetrafluoroborate; --, therefor.

In column 14, line 41, in Claim 18, delete "or" and insert -- or an --, therefor.